(12) United States Patent
Hadas

(10) Patent No.: US 6,597,944 B1
(45) Date of Patent: Jul. 22, 2003

(54) NOCTURNAL MUSCLE ACTIVITY MONITORING SYSTEM

(75) Inventor: Noam Hadas, Tel Aviv (IL)

(73) Assignee: S.L.P. Ltd., Tel Aviv (IL)

(*) Notice: Subject to any disclaimer, the term of this patent is extended or adjusted under 35 U.S.C. 154(b) by 0 days.

(21) Appl. No.: 09/869,913

(22) PCT Filed: Feb. 28, 2000

(86) PCT No.: PCT/IL00/00122
§ 371 (c)(1),
(2), (4) Date: Jul. 9, 2001

(87) PCT Pub. No.: WO00/51543
PCT Pub. Date: Sep. 8, 2000

(30) Foreign Application Priority Data

Mar. 3, 1999 (IL) .................................................. 128815

(51) Int. Cl.[7] .................................................. A61B 5/04
(52) U.S. Cl. ......................................... 600/546; 60/587
(58) Field of Search ................................ 600/546, 587, 600/590, 595, 372, 382, 383, 393, 395; 359/265–274

(56) References Cited

U.S. PATENT DOCUMENTS

| | | | |
|---|---|---|---|
| 4,427,267 A | * 1/1984 | Collins et al. | .............. 359/270 |
| 4,573,768 A | * 3/1986 | Polak et al. | ................ 359/270 |
| 4,715,367 A | 12/1987 | Crossley | |
| 5,368,042 A | 11/1994 | O'Neal et al. | |
| 5,737,114 A | 4/1998 | Bailey | |
| 5,812,300 A | * 9/1998 | Coleman | .................... 359/265 |
| 5,877,888 A | * 3/1999 | Coleman | .................... 359/265 |
| 6,117,092 A | 9/2000 | Weinstein | |
| 6,188,506 B1 | * 2/2001 | Kaiserman et al. | ......... 359/288 |

* cited by examiner

Primary Examiner—Charles A. Marmor, II
(74) Attorney, Agent, or Firm—Mark M. Friedman

(57) ABSTRACT

A muscle activity monitoring system that integrates a minimal data-collection and analysis system into a disposable, single-use device that achieves data collection and analysis without requiring the assistance of a trained technician. The monitoring system includes a muscle activity sensor for sensing muscle activity at a location on the body, and a processor for analyzing the sensed muscle activity to determine a presence of a pattern of muscle activity that is correlated to a diagnosis. The diagnosis is displayed by a plurality of non-volatile markers. The markers are preferably heat-sensitive or electrochemical cells that undergo a permanent detectable change when a current flows through the cells. A housing houses the processor, the display, and a power source on the muscle activity sensor.

15 Claims, 4 Drawing Sheets

TOP VIEW

BOTTOM VIEW

TOP VIEW

BOTTOM VIEW

Unactivated cell

Activated cell

Activated Markers

Non Activated Marker

Background

C13:11

Patient Display
√ = no problem
! = mild problem
!! = moderate problem
!!! = severe problem
X = bad study Doctors Display:
number of apnea episodes shown in 8 bit binary code Key:
1 ○    ⊘ 16
2 ○    ⊘ 32
4 ⊘    ○ 64
8 ○    ○ 128

Here the number of apnea episodes is

4+16+32=52

NOCTURNAL MUSCLE ACTIVITY MONITORING SYSTEM

FIELD AND BACKGROUND OF THE INVENTION

The present invention relates to medical monitoring devices and, in particular, it relates to a monitor for the detection of disorders of nocturnal skeletal muscle activity.

It is known that nocturnal skeletal muscle activity disorders are a common medical problem. Two such syndromes of this nature are bruxism (nocturnal teeth grinding) and Periodic Leg Movement Syndrome (PLMS).

Surveys show that over 5% of the adult population suffer from bruxism. In this condition, ongoing involuntary grinding of the teeth damages healthy enamel on the chewing surfaces of the teeth (possibly even causing stress fractures), and may cause damage to the tempero-mandibular joint. As such, Bruxism is a far more destructive process than is dental caries. However, only a minority of patients suffering from bruxism are aware of their condition. Usually, the patient is completely unaware of this disorder, and does not seek medical or dental attention until irreversible damage to their dentition has occurred necessitating extensive restorative treatment or tooth extraction. "Clenching" is a common variation of bruxism, and involves the non-purposeful closing of teeth in the chewing position. Both bruxism and clenching can occur during the day, but in most cases occur at night during sleep.

Periodic Leg Movement Syndrome (PLMS) is a common sensorimotor sleep disorder in which repeated involuntary, highly regular, jerky movements occur periodically, every 20 to 40 seconds, in one or both legs during sleep. PLMS may occur as an isolated phenomenon, but more often is associated with other sleep disorders such as Restless Leg Syndrome (RLS), narcolepsy, or sleep apnea. Surveys show that about 1% of the population over 40 years of age have either PLMS or RLS, and that the prevalence of the disorder increases with age. PLMS may also be associated with systemic diseases such as iron deficiency anemia, kidney failure, diabetes, rheumatoid arthritis, and peripheral neuropathy. PLMS and RLS may lead to severe sleep disruption and excessive daytime somnolence. As such, the patient may easily fall asleep during working hours, such as when the patient is driving a car or a truck Definitive diagnosis of bruxism can be achieved by recording jaw muscle electromyographic (EMG) signals during sleep. So too, PLMS is best diagnosed by monitoring the EMG activity of the Tibialis Anterior (calf) muscle while the patient is sleeping. Both such EMG studies are often part of an in-lab, full night, formal sleep study. In such a study, the patient is required to sleep for a whole night in a controlled environment (a "sleep laboratory") while connected to multiple monitoring devices, which continuously measure such physiological parameters as respiratory effort, nasal and oral airflow, brain electrical activity (EEG), Tibialis Anterior or jaw muscle EMG activity, heart rate and rhythm (ECG), and blood oxygen saturation. These parameters are recorded on paper or stored in a memory bank for later analysis. A trained sleep technician is required to oversee the study so as to ensure that all parameters are recorded properly. The data is then analyzed, either manually or by specialized software, to produce a "hypnogram" which describes the nature of the patients sleep. Indices in the hypnogram, such as a "bruxism index" and a "leg movement index", are then used, by a sleep specialist, to diagnose the patients pathology, and its severity.

Bruxism is initially treated with an "occlusal splint" bite guard, or by biofeedback techniques, however ongoing monitoring of the efficacy of treatment is necessary so as to determine if and when more aggressive medical or dental intervention is required. PLMS is managed with medications such as benzodiazepines, anti-dopaminergic agents, or opioids. Multiple trials of therapy may be necessary before the optimal drug and dosage is found, and a medication that is initially effective may lose its efficacy with repeated use. Thus PLMS, too, requires ongoing monitoring of the efficacy of treatment.

The formal sleep study as a means of diagnosing and following-up patients with sleep-related problems, however, suffers from several deficiencies and limitations:

1. The study requires the use of multiple medical monitoring devices and the continuous presence of a trained technician. It is thus labor intensive to perform, and requires the use of multiple, expensive, resources. As such, sleep laboratories themselves are a limited resource, each containing only a limited number of beds. This is particularly problematic as studies are often conducted on "suspicious" patients, in whom the outcome is frequently negative. In such patients, for whom there was no need for the study at all, a limited screening study may have been sufficient to exclude sleep pathology. In addition, the study price often prohibits repeating studies on a regular basis for purposes of patient follow-up, and prohibits performing multiple studies for the screening of large populations.
2. The patient is asked to sleep in an unnatural sleep environment, which may itself affect his sleep patterns.
3. The patient is inconvenienced by having to be in a hospital setting for a night.
4. There is no patient privacy.

In order to overcome some of these drawbacks, the performance of home studies by means of ambulatory systems has become popular. These studies utilize miniature ambulatory recorders, and are sometimes limited to a relatively small number of information recording channels. The patient is prepared for the study at the sleep lab, and returns home with all sensors appropriately attached. Alternatively, a technician may come to the patient's home, or the patient may attach the sensors by himself after receiving appropriate instruction from a technician. The study is then conducted in the patient's home, as he sleeps in his own bed, and the recorded data stored in a memory device. In the morning the recorder and memory device are returned to the sleep lab for data downloading to an analysis station. Some of these ambulatory systems can correct for some data recording problems, by adjusting the gain or filtering during data recording or when post-processing the data. Alternatively, the study can be monitored from the sleep lab via a modem.

Although ambulatory sleep-monitoring systems are much more convenient to the patient, and considerably less expensive than formal, in-lab, sleep studies, all current ambulatory sleep-monitoring systems suffer from several deficiencies:

1. Performance of the study still requires the participation of a trained technician (for the purposes of either attaching the monitoring device or instructing the patient how to do so) and the participation of a formal sleep laboratory (for the purposes of downloading and analyzing the test results, and maintaining the equipment necessary for the performance of the test). Such tests are thus still labor and resource intensive.
2. As analysis of the recorded data is performed off-line in the sleep laboratory, the ambulatory monitoring device must be able to store all registered data in a suitable memory storage device, until such data can be downloaded. Alternatively, if the data is relayed to the sleep laboratory in real time, a modem and telephone line are necessary. Current ambulatory devices are therefore relatively complex and expensive to manufacture. As such, ambulatory studies are still too expensive to perform on a regular basis (currently approximately $500 per study), thus precluding their widespread use as a screening tool or for purposes of frequent patient follow-up. In addition, the cost of such studies does not justify their use on "difficult" patients, such as mental health patients or small children, in whom the likelihood of technical failure of the study is high.

There is therefore a need for a nocturnal skeletal muscle activity disorder screening system that is suitable for widespread use for patient screening and follow-up. Such a system should be sufficiently simple to implement as to allow patients to perform the study at home, without the need for assistance from a trained technician. In addition, such a system should provide the patient with an easily understandable result at the end of the study, without the need for data processing at a sleep laboratory, and without the need for interpretation of the result by a physician or technician. Finally, such a system should be sufficiently inexpensive as to make multiple and frequent studies, for purposes of monitoring and follow-up, practical to finance.

SUMMARY OF THE INVENTION

The present invention is an ambulatory nocturnal muscle activity monitoring system. The invention integrates a minimal data-collection and analysis system into a disposable, single use device that achieves data-collection and analysis in real time, and outputs the study result in an easily understood format immediately following the study.

The entire system is incorporated into a single small, flexible, plastic unit which can be easily positioned, or placed, on the muscle group under study. The system is powered by a lithium, or similar, battery, which is irreversibly activated by means of the patient pulling on a tab. Once activated, electrodes input myoelectric data describing the pattern of muscle activity into a micro-processor, via an analog to digital converter. A flashing LED display indicates to the user that the device is functioning properly. A software module detects specific patterns of electromyographic activity and, together with real-time clock information, the presence of episodes of abnormal muscle activity is documented. After a predefined period of time, non volatile output flags (in the form of miniature electro-chemical cells, or heat sensitive colored dots) are set by the software, each output flag describing a specific study outcome. Once activated, the output flags undergo a permanent color change. As such, they produce an easily-read hard copy of the study results, informing the user whether significant abnormal muscle activity was detected and whether a physician need be consulted. Hereinafter, output flags which undergo a permanent change in color when activated by heat are referred to as "heat sensitive permanent color display elements", and output flags which undergo a permanent change in color when activated by an electrochemical process are referred to as "electro-chemical permanent color display elements".

The integration, onto an EMG sensor, of a muscle activity monitoring system which is capable of analyzing EMG data in real time and generating an immediate report thereof, is unique to the current invention. By "real time" is meant that the sensing of muscle activity and the processing of such sensed EMG data occur during the same time interval, or within a few seconds of each other, rather than the processing occurring after all muscle activity sensing has been completed.

As data is analyzed in real time, the need for a large memory storage unit to store data for later analysis, and the need for complex downloading hardware, are obviated. This feature allows the entire system to be manufactured in a small and inexpensive format, and provides the user with the result of the study immediately upon conclusion of the study, without the need for data processing and analysis by medical professionals at a sleep laboratory. Furthermore, as the power source, processor, and display mechanism of the device are all integrated with the EMG probe (or sensor) into a single small unit (without the need for cables or wires connecting these components to each other), and as an easily-seen flashing light confirms for the user that placement and operation of the device are correct, the device is simple and straightforward to use. The device can thus be operated without supervision by trained medical professionals. Accordingly, the cost per study is sufficiently low as to justify performing studies frequently for screening purposes (whenever there is even a slight chance of true pathology being present) or for regular patient follow-up. As there are no cables or wires connecting the EMG sensor with the rest of the device, the possibility that the sensor might be pulled off of the users body, due to the cable becoming entangled while the user is asleep, is obviated.

According to the teachings of the present invention there is provided a muscle activity monitoring system, including a muscle activity sensor, for sensing muscle activity at a location on a body; a processor, for analyzing the sensed muscle activity to determine the presence of a pattern of muscle activity, and for correlating the pattern of muscle activity with a diagnosis; a display, for displaying the diagnosis; a power source, for powering the muscle activity sensor, the processor, and the display; and a housing, for housing the processor, the display, and the power source, on the muscle activity sensor, the housing being placeable at the location on the body. There is also provided a muscle activity monitoring method, including the steps of placing a housing at a location on a body; sensing muscle activity at the housing during a time interval; processing the sensed muscle activity to detect a pattern of muscle activity, the processing occurring during the time interval; correlating the pattern of muscle activity with a diagnosis, the correlating occurring during the time interval; and displaying the diagnosis on the housing. There is also provided an electrochemical display system, including a cathode; an anode, and a layer of electro-conductive material covering at least part of the anode, the layer being operative to undergo an electrochemical process when electric current flows from the anode to the cathode, and wherein the electrochemical process eventuates in a change in a perceived color of the anode. There is further provided a method of irreversible display, including providing a cathode and an anode, the anode being at least partially covered by an electro-conductive material; inducing a flow of electrical current between the cathode and the anode, thereby effecting an electrochemical process in the electro-conductive material, and thereby causing a change in a perceived color of the anode.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a nocturnal muscle activity monitoring system.

The principles and operation of a nocturnal muscle activity monitoring system, according to the present invention, may be better understood with reference to the drawings and the accompanying description.

Figure 1:
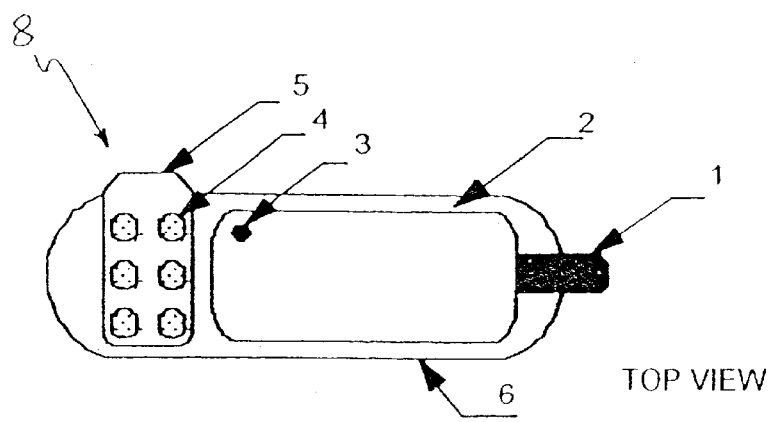
FIG. 1 is a line drawing of the physical structure of the current invention.

Referring now to the drawings, FIG. 1 is a line drawing of the physical structure of the current invention.

A muscle activity monitoring device 8 is depicted in FIG. 1. Device 8 is positioned, by the user, on the skin overlying the muscle group under study, for example the temporalis or masseter muscles (if bruxism is suspected) or the tibialis anterior muscles (if PLMS is suspected). A thin, flexible housing 6, shaped like a thin strip, serves as a base for the electronic components of device 8. In the preferred embodiment, housing 6 is made of a flexible plastic polycarbonate film approximately 0.1 mm thick, and is oval shaped. The length of housing 6 is approximately three inches and it's width one inch. A cover 2, made of a similar material as housing 6, is located on top of housing 6 so as to form a miniature box containing all hardware and electrical components of device 8. A power source (not shown), in the form of a flat lithium battery, is housed in the miniature box on housing 6, and powers the functioning of all elements of device 8. One of the contacts of the power source is insulated from a conductive electrode (not shown) on housing 6 by a pull-tab 1. When tab 1 is pulled out by the user, contact is made with the power source and the electrode, thus completing the electrical circuit, and operation of device 8 commences. Two conductive electrodes 7 and 9 are located on the opposite side of housing 6 to that of cover 2, and are covered with an adhesive gel which allows for the comfortable attachment of device 8 to the skin overlying the muscle group under study. Electrodes 7 and 9 are standard EMG electrodes (metal buttons 10 mm in diameter coated with a silver/silver-chloride ($AgCl_2$) layer) and attach to the skin by means of a pad of conductive gel, which contains water and salts. Electrodes 7 and 9 are connected to the input of an amplifier and analog-to-digital convertor and microprocessor (not shown), which are housed under cover 2. During operation of device 8, electrodes 7 and 9 sense myoelectric activity generated by the muscle group under study, whenever such muscle group contracts or relaxes. The signals so generated are processed by the microprocessor housed under cover 2, so as to detect patterns of EMG activity that are diagnostic of the muscle activity disorder being screened for (for example, bruxism or PLMS). A LED display 3 is located on cover 2 such that it can be easily seen by the user, either when looking in a mirror or when looking directly at device 8, once the system has been attached to the skin overlying the muscle group under study and operation commenced. LED 3 is operative to flash when a maximum EMG signal is detected immediately after turn-on, and thereafter flashes whenever an EMG signal over a predefined threshold (depending on the type of disorder being screened for) is detected by the microprocessor. The flashing of LED 3 indicates that proper placement of electrodes 7 and 9 has been achieved and that the system is functioning properly.

One (or more) non-volatile markers 4 are located on base 6 alongside cover 2. Together, markers 4 constitute a display component of device 8, and hereinafter, such markers are also referred to as "display elements". In a first preferred embodiment of the display component of device 8, markers 4 are electro-chemical cells which are located under gel cover 5. When current is passed through one of the cells, an electrochemical reaction induces a permanent color change in one of the electrodes. This embodiment of the display component of device 8 is described in detail in FIGS. 4, 5 and 6 below. In a second preferred embodiment of the display component of device 8, each one of markers 4 comprises a miniature heating element, and a coating of a heat sensitive material. In this embodiment, markers 4 are not covered by gel cover 5. When current is passed through one of the heating elements it heats up, inducing a change in the color of the coating material (such as rendering the coating material permanently black). This color change is permanent, even after cooling down of the element.

When the muscle activity study is complete, the microprocessor (CPU) issues a command to flow an electric current through one (or more) of non-volatile markers 4. The choice of which of markers 4 to activate depends on the study conclusion, as determined by the CPU. Each non-volatile marker 4 corresponds to one of several possible diagnoses. By "diagnoses" is meant possible study outcomes describing the pattern of abnormal muscle activity detected while the subject was sleeping. As the color change induced in marker 4 is permanent, upon awakening the user is able to immediately see the result of the study, and marker 4 serves as a permanent "hard-copy" of the result of the study.

Figure 2:
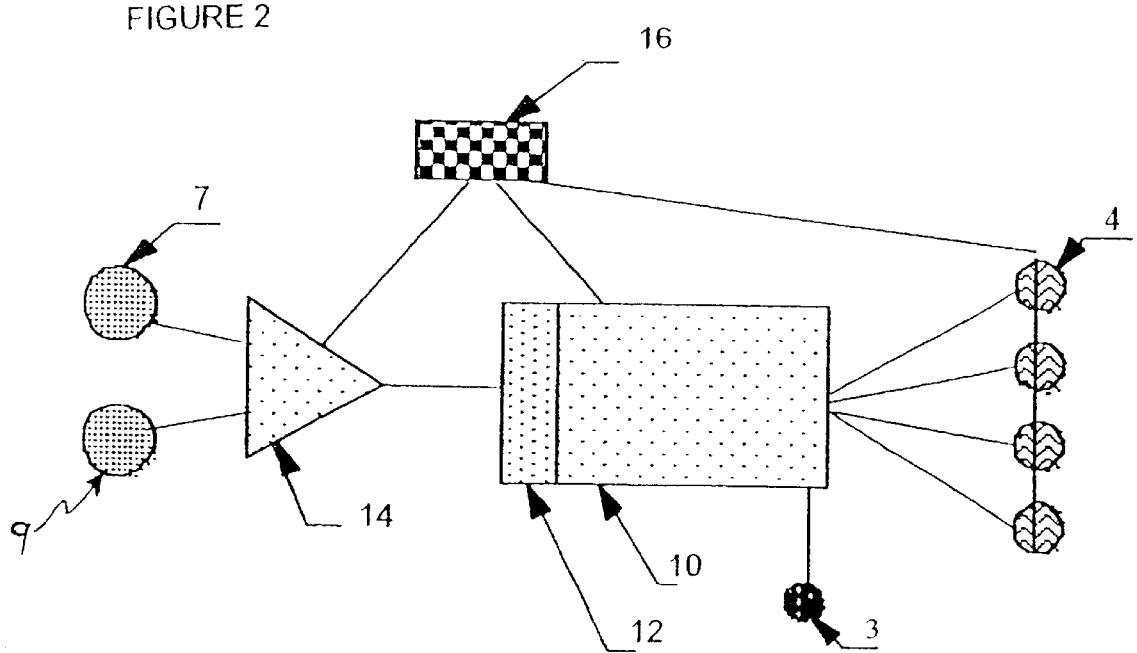
FIG. 2 is a block diagram of the electrical components of the current invention.

In FIG. 2, a simplified block diagram of the electrical components of device 8 is shown. Electrodes 7 and 9 input EMG data, in the mV range, to a band pass filter and low-noise, high gain amplifier 14 which amplifies the signal. Output from amplifier 14 is converted to a digital signal by an A/D (analog to digital) converter 12. The resultant digital data stream is input to a CPU 10, which runs specialized data acquisition and analysis software. A/D converter 12 may be part of CPU 10. CPU 10 analyses the signal in real time by taking a sample each 1 mSec, calculating the envelope amplitude of the signal, and detecting significant peaks in this value. CPU 10 causes LED 3 to flash each time a noticeable signal peak lasting over 0.5 seconds is detected. Signal maxima are counted by CPU 10 for the duration of the study, and when a conclusion is reached at the end of the study, CPU 10 outputs a command to one of non-volatile markers 4, thereby permanently changing its color. The entire device is powered by a power source 16, usually a Lithium battery.

In an alternative embodiment, a bruxing signal is derived from a strain gauge or other movement sensor located over the masseter or temporalis muscles, rather than from electrodes 7 and 9. In this embodiment, muscle bruxism exerts a force on the strain gauge, thereby changing its resistance.

The change in resistance is then used as the input data to CPU 10. In this embodiment, signal amplification and integration are not required.

Figure 3:
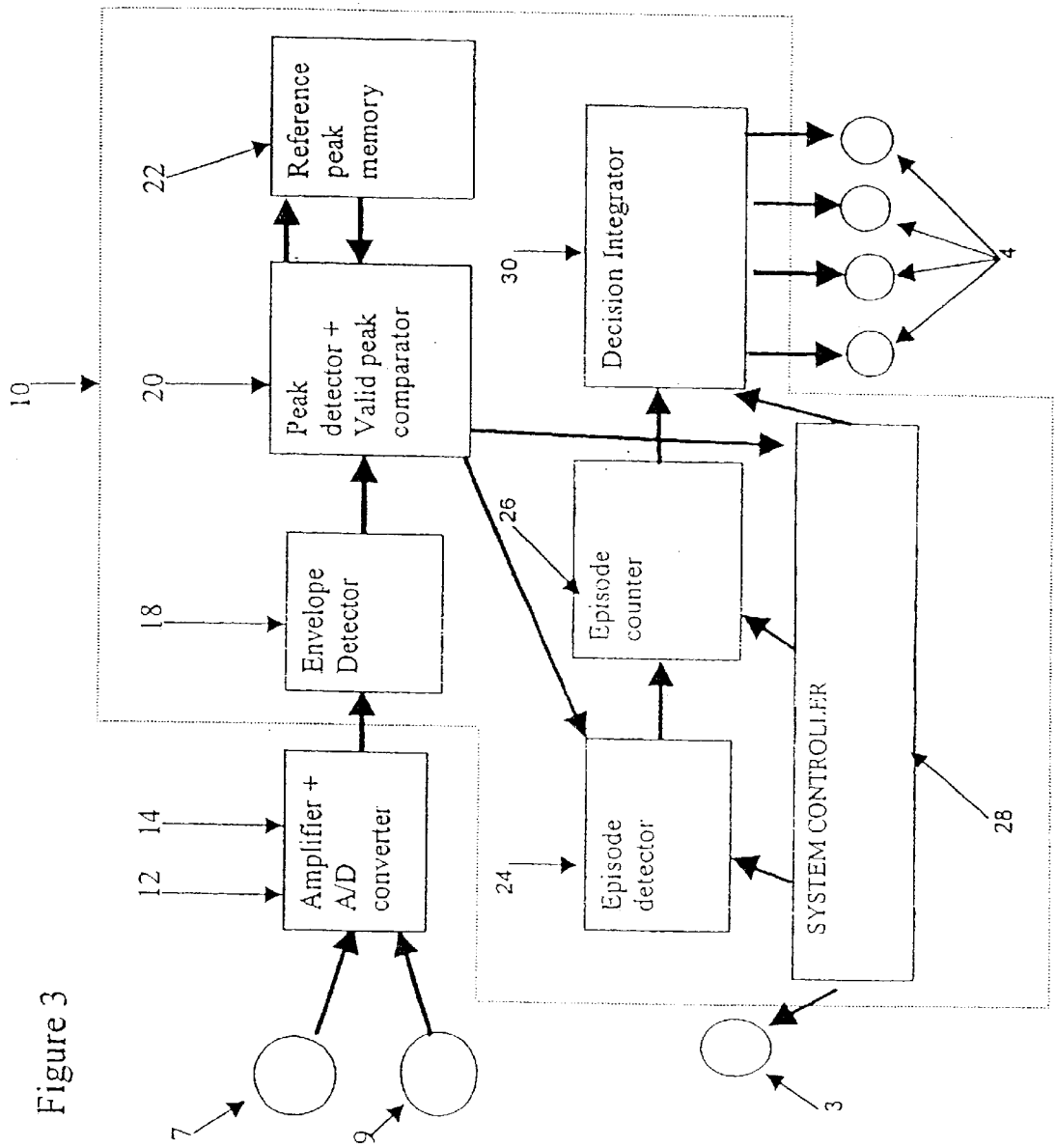
FIG. 3 is a block diagram describing the data input to, and data flow within, the CPU of the current invention.

FIG. 3 describes the data input to, and data flow within, CPU 10. Raw EMG signals from skin surface EMG electrodes 7 and 9 are smoothed, amplified and converted to digital format by amplifier 14 and A/D converter 12. Amplifier 14 and A/D converter 12 are hereinafter together referred to as a signal conditioner. The resultant digital data, reflecting total muscle activity caused by neural stimulation of the muscle, is input to an envelope detection module 18. Envelope detection module 18 calculates the envelope waveform of the high frequency components of the input data. The output from envelope detection module 18 is fed to a valid muscle contraction detection module 20. Immediately after turn-on, valid muscle contraction detection module 20 identifies a predefined pattern of maximum signal amplitude values (depending on the muscle group under study, as described below), and inputs these values to a reference peak memory 22, where such values are stored. After this initial period of reference peak value generation, valid muscle contraction detection module 20 monitors the data generated by envelope detection module 18, locates the maximum signal amplitude in the data, and compares that value to the stored reference maximum which had been measured immediately after device turn on and stored in reference peak memory 22. Sliding window integration is used for quantitative analysis of the signal and for locating maximal signal amplitude, which is compared to the maximum EMG signal sampled at turn on. An abnormal muscle contraction is marked if the signal amplitude exceeds a predefined limit (depending on the muscle group under study). For bruxism screening an abnormal muscle contraction is marked whenever the signal amplitude is at least 50% of the reference peak value. For PLMS screening, an abnormal muscle contraction is marked whenever the signal amplitude is at least 70% of the reference peak value. An episode detection module 24 calculates the time between consecutive abnormal muscle contractions, and counts the number of such contractions. If the temporal parameters of a train of contractions are within the defined limits for PLMS, one count is added to an episode counter module 26. For bruxing, a simple count of activity peaks is sufficient.

The entire study timing and duration is controlled by a system controller module 28. System controller module 28 runs a reference peak value detection loop until three distinct peaks are detected after turn-on initiates continuous data sampling thereafter, and terminates the study 5 hours after turn-on. When running the reference peak value detection loop after turn-on, system controller module 28 activates LED 3 each time a signal peak is detected, and continues doing so for a period of thirty minutes. After termination of the study, a decision integrator module 30 compares the data (describing the number and nature of abnormal muscle activity episodes detected) from episode counter module 26 to a predefined "diagnostic table", stored in decision integrator module 30, which categorizes all patterns of muscle activity episodes as falling into one of several diagnostic categories. Each diagnostic category corresponds to a particular non-volatile marker 4. A non-volatile marker 4 corresponding to the diagnostic category identified by the study is then activated by decision integrator module 30.

In normal operation, the user places device 8 over the appropriate muscle group to be screened and switches the device on by pulling out tab 1. The user then performs a reference peak value generation maneuver as follows:

When device 8 is being used to screen for bruxism or clenching, the user clenches his teeth three times as hard as possible, ensuring that LED 3 lights up with each jaw contraction.

When device 8 is being used to screen for PLMS or RLS, the user lies in bed and extends his big toe as hard as possible three times, ensuring that LED 3 lights up with each muscle contraction.

During the first 30 minutes after device 8 turn-on, CPU 10 runs a loop to identify three distinct maxima in the background EMG pattern (ignoring minor peaks occurring before and after the three distinct maxima generated by the reference peak value generation maneuver), and to integrate these three peaks so as to generate a reference peak value against which all subsequent signals will be compared. During this period of time the user goes to sleep. 30 minutes after turn-on, device 8 commences sensing and processing EMG signals, and continues to do so for approximately 5 hours. After 5 hours, the total number of abnormal muscle activity episodes (bruxing or PLMS episodes) counted is compared to a lookup table, and a determination is made as to which output flag to activate. When the tibialis anterior muscle is being monitored for the occurrence of PLMS, one of the following output flags is activated:

1. "No problem" flag—no PLMS detected.
2. "Minor problem" flag—average 1–5 PLMS episodes per hour.
3. "Moderate problem" flag—average 6–10 PLMS episodes per hour.
4. "Severe problem" flag—average over 10 PLMS episodes per hour.
5. "Bad study" flag—EMG signals where lost during the study, or were of amplitude greater than 300% of the reference peak value.

When the temporalis or masseter muscles are being monitored for the occurrence of bruxism, one of the following output flags is activated:

1. "No problem" flag—less than 20 bruxism episodes detected over 5 hours.
2. "Minor problem" flag—21 to 40 bruxism episodes detected over 5 hours.
3. "Severe problem" flag—more than 40 bruxism episodes detected over 5 hours.
4. "Bad study" flag—EMG signals where lost during the study, or were of amplitude greater than 300% of the reference peak value.

A similar lookup table describing the occurrence of clenching, rather than bruxism, may also be incorporated into device 8.

Upon awakening, the user reads the result of the study. As the markers retain their appearance indefinitely, the device can be kept indefinitely as a medical record, and test results can be compared from study to study.

The average signal amplitude for nocturnal clenching is usually at least 50% greater than the reference peak value (which was measured during maximal voluntary clenching), and the average signal amplitude for bruxism is usually at least 20% greater than the reference peak value. Thus, masseter or temporalis signals which are between 15% and 40% greater than the reference peak value for more than a minimal duration (such as 0.5 seconds) will be identified as bruxism episodes, and signals which are more than 40% greater than the reference peak value will be identified as clenching episodes.

The average signal amplitude for PLMS is usually at least 30% greater than the reference peak value measured during maximum voluntary toe extension. Thus, tibialis anterior signals which are at least 30% greater than the reference peak value for more than a minimal duration (such as 0.5 seconds) will be identified as abnormal events, and the occurrence of at least 3 such events within 40 seconds will be counted as one PLMS episode. Normal adults usually have less than 5 episodes per hour during sleep.

Figure 4:
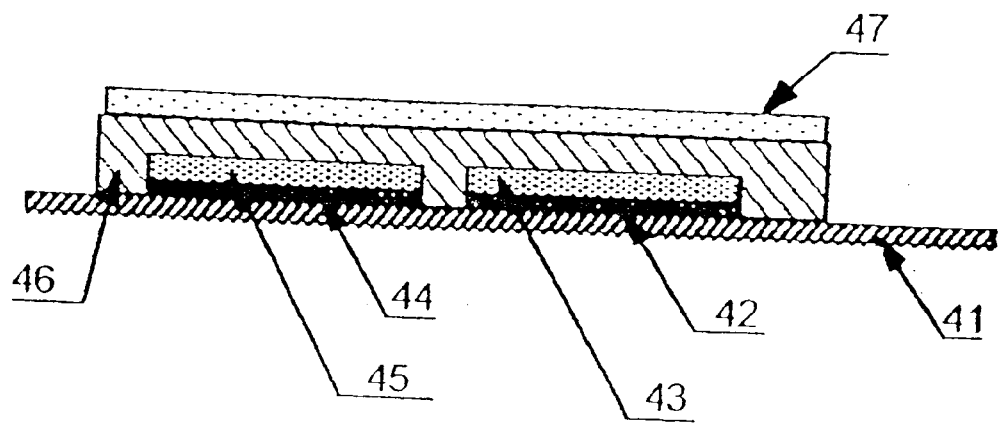
FIG. 4 is a cross-section through an unactivated electrochemical display unit suitable for use in the current invention.
Figure 5:
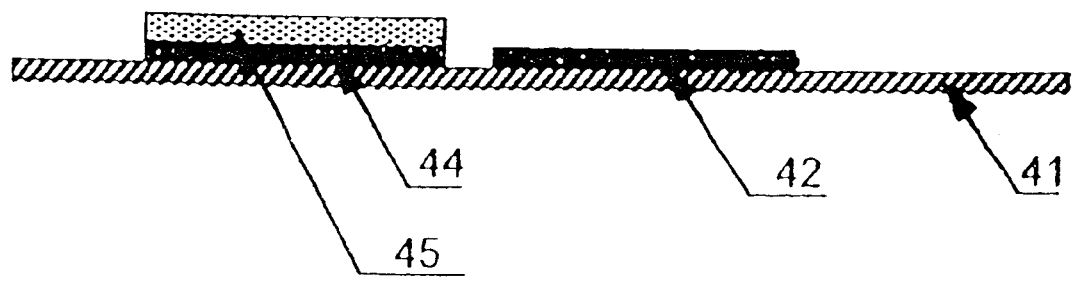
FIG. 5 is a cross-section through an activated electrochemical display unit suitable for use in the current invention.

FIGS. 4, 5 and 6 describe a preferred embodiment of the display component of device 8. In this embodiment, each display element 4 is an electro-chemical cell. An electro-chemical reaction occurring in the cell causes a change in appearance of one or more electrodes of the cell. As that electrode is visible to the user, the color change serves to convey information to the user. By varying the shape and number of electrodes, display cells of this type can be constructed so as to convey a wide variety of display messages.

The method of this embodiment of the display component of device 8 is based on electroplating, electro-stripping or otherwise changing the appearance of an electrode in an electro-chemical cell, under the influence of a weak electrical current (a current of only a few micro-Amperes, at a voltage of less than 3V, is sufficient to remove several microns of metal off an area of several square millimeters, and thus create a noticeable color change). The process takes place in a solid gel environment (gel cover 5). The gel environment consists of a polymeric gel containing electrolytes to facilitate current transfer through the gel and otherwise complete the chemical reaction that needs to take place inside the cell.

FIG. 4 is a schematic depiction of a cross-section through an electro-chemical display cell. The display cell comprises a base material 41, such as a polycarbonate film, onto which a conductive copper layer is laminated. The copper layer can be shaped, using standard Printed Circuit Board (PCB) manufacturing techniques well known in the art (such as photolythograpy and acid etching), into any desired character or symbol, depending on the nature of the information to be depicted on the display. The copper layer comprises two separate elements—one being a message-bearing element 42, and the other a current-collecting element 44. In a typical configuration message-bearing element 42 has dimensions of 2 by 4 mm, and current-collecting element 44 has dimensions of 3 by 12 mm.

Two layers 43 and 45 of an electro-conductive material such as tin (Sn) solder are plated onto copper elements 42 and 44 respectively, using standard PCB manufacturing techniques (such as electroplating or electroless plating), so as to achieve a thickness of layers 43 and 45 of at least 0.1–0.5 micrometers. A layer of polymeric conductive gel 46 covers base material 41 and solder layers 43 and 45. Gel layer 46 is 1–3 mm thick, is a polymer of the PVA family, and contains small amounts of NaCl, KCl and/or other inorganic salts. An optional layer of conductive aluminum foil 47 covers gel layer 46, and serves to increase the display cell's conductivity.

Activation of the display cell is achieved by applying a low voltage source (approximately 3V DC) across copper elements 42 and 44. The positive terminal of the voltage source is connected to message-bearing element 42, and the negative terminal of the voltage source is connected to current-collecting element 44. Copper elements 42 and 44 thus function as electrodes of an electro-chemical cell, with element 42 being the anode, and element 44 being the cathode of the cell. As electric current begins to flow from element 42 to element 44, solder layer 43 begins to dissolve into gel layer 46 off of message-bearing element 42. Initially, over the course of several minutes, the solder of solder layer 43 tarnishes, becoming covered with the black layer of the oxide. Thereafter, once current flow ceases, and depending on the exact composition of gel layer 46, the oxide dissolves into gel layer 46, eventually exposing the red color of copper element 42. If, however, gel layer 46 is removed when current flow ceases, the oxide does not dissolve.

The electrochemical reaction occurring in the display cell is as follows:

At the Anode (+):

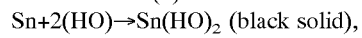

At the Cathode (−):

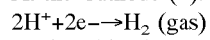

During this electrochemical process, copper element 44 remains plated by solder layer 45, thus serving as a reference color enhancing the readability of the color change induced on message-bearing element 42. Current is then terminated and gel layer 46 removed, so as to expose message-bearing element 42 and allow the user to read the information depicted on the display cell. In this exposed state the cell can be kept indefinitely. Alternatively, if gel layer 46 is transparent and is of such composition that oxide doesn't dissolve into it, then readout can be done and the display kept without removing gel layer 46 off of the display.

In an alternative embodiment of the display component of device 8, copper element 42 is not initially coated by solder layer 43, but rather, as current flows from element 42 to 44, element 42 becomes plated with a conductive material extracted from gel layer 46 in an electroplating process, thereby rendering a color change in element 42.

FIG. 5 is a schematic depiction of a cross section through the activated display cell after the user has removed gel layer 46.

Figure 6A:
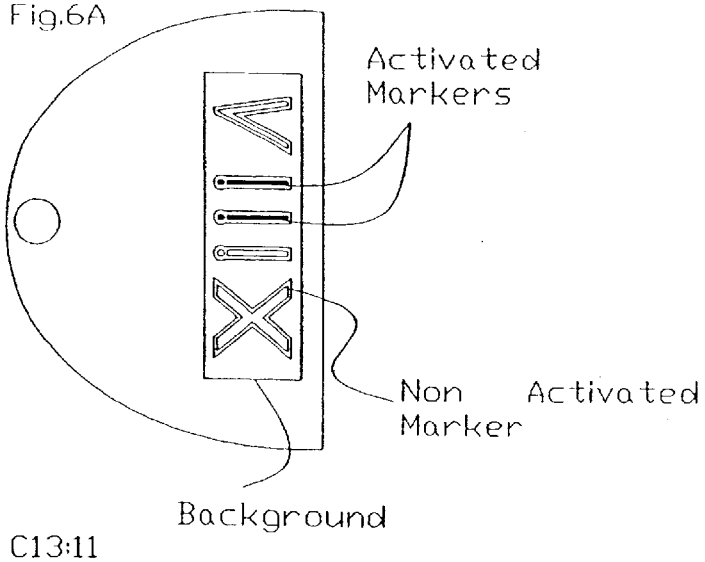
FIG. 6 is a line drawing of two electrochemical display units, demonstrating possible formats for displaying study outcomes.
Figure 6B:
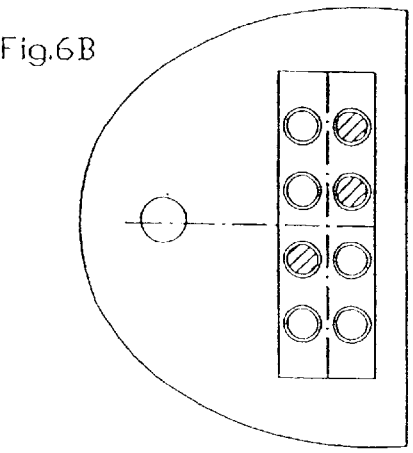

FIG. 6 is a line drawing of the external appearance of two electro-chemical display units, as described in the current invention. Two of several possible formats for displaying study outcomes are shown. In FIG. 6A a format suitable for use when a patient, rather than a doctor, will read the study outcome is shown. As illustrated, the display shows that a "moderate" problem had been detected by the device. In FIG. 6B a format suitable for use when a doctor will read the study outcome is shown. As illustrated, the display shows that 52 bruxing episodes had been detected by the device.

The silver colored Sn coating of message-bearing element 42 tarnishes to dark gray after approximately 20 minutes of current flow. Thereafter, if current flow is discontinued, the coating dissolves fully into gel layer 46 over the course of several hours, thus fully exposing the underlying copper of message bearing element 42. As the red copper color of message bearing element 42 actually provides poorer contrast against the silver-colored coating of element 44 than does the tarnished dark gray color of Sn layer 43, a small "maintenance current" may be passed though the cell (either as a small DC current, or as pulses with low duty cycle, at approximately 1% of the activation current), so as to prevent the coating from dissolving fully into gel layer 46. Voltage of this maintenance current may be maintained until the gel layer is peeled off to read the display, or until the battery runs out.

The display cell described above is thus a non-volatile, single use, micro-power, non-erasable display, which may be suitable for any application where very low quantities of information are to be displayed to the user and then kept permanently as a record of the result. Display cells of this nature could thus be used in multiple monitoring devices, such as devices used to monitor acceleration or temperature of a cargo shipment (so as to determine if the shipment had been exposed to shock or high temperatures while in transit), and medical devices in which the user is informed of a negative or positive test result. Electro-chemical displays of the type described in the current invention overcome drawbacks of existing display technologies such as LED and LCD displays (which require ongoing power to operate) and electromechanical flags (which are relatively big and heavy, and are limited to the display of only one or two bits of data).

It will be appreciated that the invention as described herein may be supplemented in several ways, without departing from the spirit of the invention. For example, a heat sensitive element, to sense skin temperature during the study, may be incorporated into device 8. This element would indicate if the device had been removed during the night, prior to the end of the study. In addition, a light sensor may be incorporated into device 8 so as to determine that the lights were switched off during the study, as a fraud detection mechanism. A further addition to device 8 may be a circuit and appropriate software that monitor the DC resistance between electrodes 7 and 9. With placement of electrodes 7 and 9 on the skin of the user the circuit is completed, inducing flow of a small current. Such a circuit can therefore be used to automatically switch on the electronic components of device 8, when a current of over a predefined minimum is detected. This would eliminate the need to manually turn on device 8 by pulling tab 1. The same circuit can also be used to detect if device 8 was removed, or if the skin contact of electrodes 7 and 9 was intermittent or defective, during the study.

It will be further appreciated that the technique of integrating a minimal data analysis system onto a sensor, such that sensed data is analyzed in real time, and an easily understood study report is immediately generated (as described in the current invention with regard to the sensing of abnormal nocturnal muscle activity), can be applied to screening devices for a variety of medical conditions. Some examples of possible monitoring devices which share this technique of data analysis and explication, but which sense different physiological parameters, are:

1. A nocturnal tremor sensor, which could aid in the titration of anti-tremor medication in patients with Parkinsons disease or other neuro-motor disorders.
2. A sensor for the detection of sweat during the night, which could aid in the titration of medication for night sweating, and help diagnose and treat night sweating due to hormone deficiency, night terrors, diabetes, or other reasons.
3. A night breath-sounds monitor, or nocturnal cough counter, for asthma management.
4. A sensor for the detection of body temperature during the night, which could aid in the titration of medication for menopausal heat flashes.
5. A sensor for the detection of breathing movements, which could aid in the long term follow up of asthma by counting total movements during a set period.
6. A sensor for the detection of gross body movement during the night, to help in the long term treatment and follow up of syndromes such as head banging and body rocking.
7. A sensor for the detection of bladder muscle activity, to help diagnose and titrate medications for "Detrusor muscle instability" in women.

All the above mentioned applications of the current invention are intended for use as screening modalities, rather than as definitive diagnostic tests for the relevant illnesses.

There has thus been described a nocturnal muscle activity disorder screening system which can be easily and reliably used without the need for professional supervision or the use of complex data storage and analysis hardware. The system is sufficiently simple and inexpensive as to facilitate performance of multiple studies on the same patient, on unreliable patents, or on patients with a low likelihood of having real pathology. The system allows the study to be performed in the patients natural sleep environment, and does not infringe patient privacy.

What is claimed is:

1. A muscle activity monitoring system, comprising
   a) a muscle activity sensor, for sensing muscle activity at a location on a body;
   b) a processor, for analyzing said sensed muscle activity to determine the presence of a pattern of muscle activity, and for correlating said pattern of muscle activity with a diagnosis of a disorder;
   c) a display, for displaying said diagnosis;
   d) a power source, for powering said muscle activity sensor, said processor, and said display; and
   e) a housing, for housing said processor, said display, and said power source, on said muscle activity sensor, said housing being placeable at said location on said body.

2. The system of claim 1, wherein said muscle activity sensor include an electromyograph electrode.

3. The system of claim 2, wherein said pattern of muscle activity is a frequency of electromyographic signals of amplitude greater than a reference amplitude.

4. The system of claim 1, wherein said location is selected from the group comprising the location of the temporalis muscle, the location of the masseter muscle and the location of the tibialis anterior muscle.

5. The system of claim 1, wherein said diagnosis is selected from the group comprising a degree of severity of bruxism, a degree of severity of restless leg syndrome, and a degree of severity of paroxysmal leg movement syndrome.

6. The system of claim 1, wherein said power source is a battery.

7. The system of claim 1, wherein said display is selected from the group comprising heat-sensitive permanent color display elements and electro-chemical permanent color display elements.

8. The system of claim 1, wherein said housing is a flexible plastic unit.

9. The system of claim 1, wherein said processor comprises
   a) an analog to digital converter, for converting a signal describing said sensed muscle activity into a digital signal;
   b) an envelope detector, for detecting signals, in said digital signal, describing episodes of muscle activity;
   c) a valid muscle contraction detector, for determining a reference amplitude for said detected signals describing episodes of muscle activity, and for comparing said detected signals describing episodes of muscle activity to said reference amplitude so as to detect episodes of potentially abnormal muscle contraction;
   d) a reference peak memory, for storing said reference amplitude;
   e) an episode detector, for detecting episodes of abnormal muscle contraction by calculating a temporal relationship between said episodes of potentially abnormal muscle contraction and by counting said episodes of potentially abnormal muscle contraction;
   f) an episode counter, for counting said detected episodes of abnormal muscle contraction;

g) a decision integrator, for
  i) generating a description of a pattern of muscle activity from said counted detected episodes of abnormal muscle contraction,
  ii) correlating said described pattern of muscle activity with a diagnosis, and
  iii) informing said display to display said diagnosis, and
h) a system controller, for initiating and terminating operation of said analog to digital converter, said envelope detector, said valid muscle contraction detector, said reference peak memory, said episode detector, said episode counter and said decision integrator.

10. A muscle activity monitoring method, comprising the steps of
  a) placing a housing at a location on a body;
  b) sensing muscle activity at said housing during a time interval;
  c) processing said sensed muscle activity to detect a pattern of muscle activity, said processing occurring during said time interval;
  d) correlating said pattern of muscle activity with a diagnosis of a disorder, said correlating occurring during said time interval; and
  e) displaying said diagnosis on said housing.

11. The method of claim 10, wherein said location is selected from the group comprising a location of the temporalis muscle, a location of the masseter muscle and a location of the tibialis anterior muscle.

12. The method of claim 10, wherein said muscle activity is sensed as an electromyographic signal.

13. The method of claim 10, wherein said processing and said correlating are achieved by a processor located on said housing.

14. The method of claim 10, wherein said displaying is achieved by inducing a permanent color change in a display element on said housing.

15. The method of claim 10, wherein said housing is a flexible plastic unit.

* * * * *